United States Patent [19]

Wegener et al.

[11] 4,375,436

[45] Mar. 1, 1983

[54] CONTINUOUS PROCESS FOR THE PRODUCTION OF CHLOROALKYL-SULFONYL ISOCYANATES

[75] Inventors: Peter Wegener, Königstein; Wilhelm Riemenschneider, Frankfurt am Main; Dieter Ulmschneider, Königstein, all of Fed. Rep. of Germany

[73] Assignee: Hoechst Aktiengesellschaft, Frankfurt am Main, Fed. Rep. of Germany

[21] Appl. No.: 324,873

[22] Filed: Nov. 25, 1981

[30] Foreign Application Priority Data

Nov. 28, 1980 [DE] Fed. Rep. of Germany ....... 3044980

[51] Int. Cl.³ .......................................... C07C 119/042
[52] U.S. Cl. ................................................ 260/545 R
[58] Field of Search .................................... 260/545 R

[56] References Cited

FOREIGN PATENT DOCUMENTS 1226565 10/1966 Fed. Rep. of Germany.
1230016 12/1966 Fed. Rep. of Germany.
1146628  3/1969 United Kingdom.

OTHER PUBLICATIONS

Graf, Angew. Chem. 80, p. 187 (1968).
Günther et al., Chem. Ber. 103, pp. 663-669, (1970).

*Primary Examiner*—Dolph H. Torrence
*Attorney, Agent, or Firm*—Curtis, Morris & Safford

[57] ABSTRACT

The invention relates to a process for the production of chloroalkylsulfonyl isocyanates of the formula

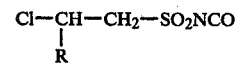

by a catalytically induced reaction of chlorosulfonyl isocyanate with one or more $C_2$-$C_4$-olefins. The reaction is carried out in a continuous manner in a tubular reactor.

7 Claims, No Drawings

CONTINUOUS PROCESS FOR THE PRODUCTION OF CHLOROALKYL-SULFONYL ISOCYANATES

A process for the production of chloroalkylsulfonyl isocyanates by a catalytically induced reaction between olefins and chlorosulfonyl isocyanate has already been disclosed in German Patent Specification 1,211,165.

The reaction is carried out without the use of pressure and its space-time conversion is limited by the rate at which the heat produced in the reaction can be dissipated. (D. Günther, F. Soldan, Chem. Ber. 103, 663 (1970) and Angew. Chem. 80, page 187 (1968).) If the reaction is carried out in relatively large batches, considerable fluctuations in yield and conversion occur, which cannot be eliminated by the customary measures, such as more vigorous stirring, improved heat dissipation and metering of the catalyst.

The object was therefore to overcome this unreliable course of reaction and to develop a process, by means of which the production of the desired substances with a constantly good yield and conversion would be made possible also on a larger, industrial scale.

At first, packed trickling columns and a bubble column were investigated as possible reactors, but they turned out to be far worse in conversion and yield than the batchwise process. In particular, in these trials the content of the 1:2 adduct, as an undesirable by-product, namely the 3-oxo-2-(2-chloroethyl)-isothiazolidine-1,1-dioxide, increased by over 20%, relative to the content of the desired 1:1-adduct, and in the case of the bubble column, backmixing and transverse mixing of the reaction flow occured, which made it impossible to have a uniform concentration of catalyst, controlled in space and time.

It has been found to be possible, surprisingly, to reduce the content of this byproduct, to control the reaction exactly and to obtain a high yield, by carrying the reaction out in a continuous manner and using a long tube as reaction vessel, into which chlorosulfonyl isocyanate, the olefin and the catalyst are introduced and reacted.

The invention thus relates to a process for the production of chloroalkylsulfonyl isocyanates of the formula

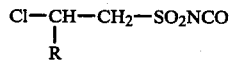

in which R denotes hydrogen, methyl or ethyl, by a catalytically induced reaction of chlorosulfonyl isocyanate with one or more $C_2$-$C_4$-olefins, which comprises carrying out the reaction in a continuous manner in a tubular reactor.

Possible catalysts are all compounds which are able to create free radicals under the reaction conditions, such as, for example, peroxide or azo compounds. Azo-bis-isobutyronitrile, dialkyl-peroxydicarbonates or benzoyl peroxide may be mentioned in particular. The catalyst is used in general in amounts of 0.01 to 20% by weight, relative to chlorosulfonyl isocyanate. The total amount of catalyst can be added all at once at the inlet end of the reactor, but it is also possible to divide the total amount of catalyst and to add these partial amounts, which can differ in size, to the tubular reactor at different points. Olefin and chlorosulfonyl isocyanate can be passed through the reactor cocurrently or countercurrently; the cocurrent method is preferred.

In contrast to the previously known method, where a constant concentration of catalyst is maintained during the whole reaction by a uniform rate of addition, this way of adding the catalyst causes the concentration of catalyst to fluctuate strongly during the course of the reaction in this process. It was therefore surprising to find that, when employing a continuous method, yields as high or even higher than in the case of the discontinuous method are obtained nevertheless.

The reaction is carried out at an elevated temperature, a range between 60° and 80° having proved advantageous. Which temperature is optimum for a particular case depends primarily on the catalyst used and its decomposition temperature.

The ratio of diameter to length for the tubular reactor employed in the reaction should be between 1:100 and 1:10,000. A diameter to length ratio of 1:500 to 1:4,000 is preferred. The residence time in the tube is optimally 1-3 hours, but shorter times down to ½ an hour and longer times up to 8 hours are possible. The pressure in the tubular reactor is between 1 and 5 bar. This process does not require use of a solvent or diluent. It is certainly possible to react not only one but two or three different olefins with chlorosulfonyl isocyanate. This can be effected by passing in the olefins either simultaneously or successively. In any case, a mixture of the corresponding chloroalkylsulfonyl isocyanates is obtained in this reaction.

The reaction proceeds advantageously, if the olefin is employed in a certain excess of approx. 10% more than the stoichiometrically required amount. Under these conditions, ethylene has a selectivity of approx. 85% to 50% conversion, and propylene has the same selectivity at over 90% conversion. The proportion of the 2:1 adduct is here below 5%.

Chlorosulfonyl isocyanates produced according to the invention are valuable intermediate products. For example, they can be reacted with stearylamine to prepare a leather auxiliary.

The advantage of the process according to the invention is that the reaction is carried out in a completely enclosed apparatus with a small reactor capacity. This makes handling the very moisture-sensitive isocyanates more reliable, and the degree of discomfort experienced by the operating personnel is lowered considerably. That a diluent can be omitted and the pressure reduced are also further technical advantages compared with the previously employed process.

EXAMPLE 1-7

(see Table 1)

Polytetrafluoroethylene (PTFE) tubing or a stainless steel (V4A) tube with an internal diameter of 5 or 10 mm and a length of 4, 10, or 20 m, wound in the form of a coil, is warmed in a heating bath. Chlorosulfonyl isocyanate and a solution of the catalyst in chlorosulfonyl isocyanate are pumped in together. Ethylene is injected at the tube inlet and the pressure is adjusted via a reducing valve. The product is discharged through a regulating valve at the outlet end of the tube. The analytical values are percentage areas determined by gas chromatography and they correspond approximately to percentages by weight.

TABLE 1

| Example | Tube dimensions φ mm | Length mm | Material | Packing | φ/Length | CSI ml/h | Catalyst concentration Mol % | Residence time h | Temp. °C. | Pressure bar | % area by gas chromotography analysis Clesi % | 2:1 adduct % |
|---|---|---|---|---|---|---|---|---|---|---|---|---|
| 1 | 5 | 10000 | PTFE | 50 | 1/2000 | 25 | IPPC 0.35 | 2 | 75 | 2 | 39 | 8 |
| 2 | 5 | 10000 | V4A | 50 | 1/2000 | 50 | IPPC 0.35 | 1 | 75 | 2 | 31 | 3 |
| 3 | 5 | 10000 | PTFE | 50 | 1/2000 | 50 | EHPC 0.35 | 1 | 75 | 2 | 56 | 10 |
| 4 | 5 | 20000 | " | 100 | 1/4000 | 50 | NBPC 0.35 | 2 | 75 | 2 | 57 | 7 |
| 5 | 5 | 10000 | V4A | 50 | 1/2000 | 50 | IPPC 0.35 | 1 | 75 | 16 | 25 | 13 |
| 6 | 10 | 4000 | " | 100 | 1/400 | 100 | IPPC 0.35 | 1 | 75 | 2 | 10 | 1.7 |
| 7 | 10 | 4000 | " | 100 | 1/400 | 50 | IPPC 0.35 | 2 | 65 | 8 | 16 | 10 |

CSI = chlorosulfonyl isocyanate
IPPC = isopropyl peroxydicarbonate
EHPC = ethylhexyl peroxydicarbonate
NBPC = n-butyl peroxydicarbonate
Clesi = chloroethylsulfonyl isocyanate
PTFE = polytetrafluoroethylene

EXAMPLE 8–13

(see Table 2)

An apparatus which is composed of a glass coil of approx. 1 cm internal diameter and about 9 m length with a capacity of approx. 7 l, is heated to 70° C. by an oil circulating around it. Chlorosulfonyl isocyanate and the catalyst were pumped in separately, and ethylene or propylene were passed in cocurrently through a constant-pressure valve. The catalyst was added in two partial amounts at the inlet of the reactor at the bottom and in the middle. The reaction product was let down at the upper reactor outlet and separated from excess olefin in a separator. The chloroalkylsulfonyl isocyanate flows from the bottom of the separator and, depending on requirements, it can be further reacted in the form in which it is obtained or it can be purified by distillation. The analyses were carried out in the middle and at the top reactor outlet. The analytical values are percentage areas determined by gas chromatography and correspond approximately to percentages by weight.

Example 10 shows that countercurrent flow of gas and liquid does not produce better results than cocurrent flow.

EXAMPLE 14 AND 15

1.0 kg of chlorosulfonyl isocyanate, 10 g of n-butyl peroxydicarbonate as a catalyst and ethylene under a pressure of 2 bar were fed in hourly at a temperature of 70° C. at the lower inlet point as in Example 9 of the tubular reactor described in Examples 8–13. Propylene under a pressure of 2 bar and a further amount of 10 g of n-butyl peroxydicarbonate as catalyst were introduced into the middle of the reactor. The composition of the reaction mixture at the outlet was found to be analytically as follows: 7.2% of chorosulfonyl isocyanate, 41.3% of chloroethylsulfonyl isocyanate, 44.1% of chloropropylsulfonyl isocyanate and 3.9% of the 2:1 adduct.

If ethylene and propylene are added simultaneously under a pressure of 2 bar at the inlet of the reactor, the following composition of the mixture at the outlet is obtained: 5.3% of chlorosulfonyl isocyanate, 19.3% of chloroethylsulfonyl isocyanate, 67% of chloropropylsulfonyl isocyanate and 3.7% of 2:1 adduct.

EXAMPLE 16

1-Butene under a pressure of 1 bar was reacted analogously with 2 kg/h of chlorosulfonyl isocyanate and 2×10 g/h of n-butyl peroxydicarbonate as catalyst at a temperature of 70° C. in the tubular reactor described in the preceding examples. The discharge had the following composition: 43.6% of chlorosulfonyl isocyanate, 37.3% of 2-chlorobutanesulfonyl isocyanate and 1.9% of 2:1 adduct.

TABLE 2

| Example | Direction of flow | CSI kg/h | NBPC Catalyst g/h | Temp. °C. | Pressure bar | Reaction time h | Total amount of CSI used kg | Sample point | Percent area by gas chromotography analysis CSI % | Clesi % | 2:1 adduct % |
|---|---|---|---|---|---|---|---|---|---|---|---|
| Ethylene + CSI | | | | | | | | | | | |
| 8/1 | cocurrent | 3.0 | 2 × 20 | 70 | 2 | 5 | 16.0 | Middle | 52.4 | 36.5 | 2.2 |
| /2 | | | | | | | | Top | 45.4 | 44.1 | 2.3 |
| /3 | " | 3.0 | 2 × 20 | 70 | 2 | 6 | 19.0 | Top | 51.2 | 39.7 | 2.2 |
| 9/1 | " | 1.8–2.0 | 2 × 10 | 70 | 2 | 7 | 13.0 | Middle | 52.6 | 37.9 | 4.9 |
| /2 | | | | | | | | Top | 45.6 | 45.1 | 4.5 |

TABLE 2-continued

| Example | Direction of flow | CSI kg/h | NBPC Catalyst g/h | Temp. °C. | Pressure bar | Reaction time h | Total amount of CSI used kg | Sample point | | Percent area by gas chromotography analysis | |
|---|---|---|---|---|---|---|---|---|---|---|---|
| 10/1 /2 Propylene + CSI | counter-current | 1.8–2.0 | 2 × 10 | 70 | 2 | 6 | 13.0 | Middle Bottom | 74.7 57.3 | 19.0 33.0 Me—Clesi | 1.7 4.3 |
| 11/1 /2 | cocurrent | 3.0 | 40 | 70 | 2 | 5.5 | | Middle Top | 19.1 7.8 | 72.8 83.0 | 1.5 1.3 |
| 12/1 /2 | " | 2.0 | 40 | 70 | 2 | 6 | | Middle Top | 4.0 0.9 | 83.4 87.2 | 2.6 3.1 |
| 13/1 /2 /3 /4 /5 /6 | " " " | 2.0 " " | 40 " " | 70 " " | 2 " " | 46.5 " " | 95.5 " " | Middle Top Middle Top Middle Top | 15.8 6.3 19.3 0.4 11.7 7.0 | 75.5 81.8 72.5 81.3 75.8 83.9 | 1.7 3.6 1.4 2.8 2.4 2.7 |

Me—Clesi = β-chloropropylsulfonyl isocyanate

We claim:

1. A process for the production of chloroalkylsulfonyl isocyanates of the formula

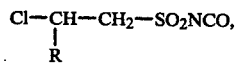

in which R denotes hydrogen, methyl or ethyl, by a catalytically induced reaction of chlorosulfonyl isocyanate with one or more $C_2$–$C_4$-olefins, which comprises carrying out the reaction in a continuous manner in a tubular reactor.

2. A process as claimed in claim 1, wherein the reaction is carried out in a tubular reactor for which the ratio of diameter to length of the tubes is 1:100 to 1:10,000, preferably 1:500 to 1:4,000.

3. A process as claimed in claim 1, wherein the reaction is carried out at a pressure of 1 to 5 bar.

4. A process as claimed in claim 1, wherein the catalyst is introduced into the tubular reactor at several points, as appropriate in differing amounts.

5. A process as claimed in claim 1, wherein the reaction is carried out at temperatures between 60° and 80°.

6. A process as claimed in claim 1–5, wherein olefins and chlorosulfonyl isocyanate are passed through the reactor co-currently.

7. A process as claimed in claim 1, wherein ethylene and propylene are metered into the reactor either simultaneously or successively.